(12) United States Patent
Bhalla

(10) Patent No.: US 7,832,019 B1
(45) Date of Patent: Nov. 16, 2010

(54) STERILE GLOVE WITH TOUCHLESS DONNING

(76) Inventor: Jagmohan Bhalla, 2022 Columbia Rd. NW., #605, Washington, DC (US) 20009

( * ) Notice: Subject to any disclaimer, the term of this patent is extended or adjusted under 35 U.S.C. 154(b) by 0 days.

(21) Appl. No.: 12/635,300

(22) Filed: Dec. 10, 2009

(51) Int. Cl.
*A41D 19/00* (2006.01)

(52) U.S. Cl. ............................................. 2/160; 2/162

(58) Field of Classification Search ................ 2/16, 2/158, 159, 160, 161.6, 161.7, 162, 170; 128/878, 879; 223/111
See application file for complete search history.

(56) References Cited

U.S. PATENT DOCUMENTS

| 4,002,276 | A | | 1/1977 | Poncy et al. |
| 4,069,913 | A | | 1/1978 | Harrigan |
| 4,155,494 | A | | 5/1979 | Poncy et al. |
| 4,159,069 | A | | 6/1979 | Poncy et al. |
| 4,868,927 | A | * | 9/1989 | Bourdeau et al. ............ 2/161.1 |
| 4,898,309 | A | | 2/1990 | Fischer |
| 6,061,833 | A | * | 5/2000 | Smith et al. ..................... 2/162 |
| 6,435,388 | B1 | | 8/2002 | Binder et al. |
| 6,832,708 | B2 | | 12/2004 | Sinai |
| 7,527,181 | B1 | * | 5/2009 | Sullivan ..................... 223/111 |
| 2007/0061942 | A1 | | 3/2007 | Schrodl |

* cited by examiner

*Primary Examiner*—Katherine Moran
(74) *Attorney, Agent, or Firm*—Squire, Sanders & Dempsey, LLP

(57) ABSTRACT

A sterile glove includes a hand and finger portion and a cuff having an inside surface and an outside surface. The cuff is adapted to be folded over at a fold when the glove is packaged in a sterile package and the fold forms an opening for inserting a hand into the glove. A stretching mechanism is coupled substantially near or on the fold and is adapted to increase a size of the opening while donning the glove. At least a portion of the stretching mechanism is detachable. The stretching mechanism has an unstretched state and a stretched state, and the stretching mechanism is in the unstretched state when the glove is packaged.

15 Claims, 5 Drawing Sheets

STERILE GLOVE WITH TOUCHLESS DONNING

FIELD OF THE INVENTION

One embodiment is directed generally to a sterile glove, and in particular to a sterile glove that allows for touchless donning.

BACKGROUND INFORMATION

Sterile elastomeric gloves are used with increasing frequency by medical and laboratory professionals to prevent the tactile transfer of foreign materials during various procedures. Sterile gloves are typically packaged with their cuffs folded over to expose a portion of the inner surface of the cuff. This allows the gloves to be picked up and held during donning by touching only the area close to the fold and at some distance from the cuff rim, which minimizes the risk of contamination.

Various packaging and dispenser improvements and techniques have been introduced to address the problems of sterile glove donning. However, these known methods tend to unnecessarily increase the cost and complexity of use and manufacture of the gloves.

SUMMARY OF THE INVENTION

One embodiment is a sterile glove that includes a hand and finger portion and a cuff having an inside surface and an outside surface. The cuff is adapted to be folded over at a fold when the glove is packaged in a sterile package and the fold forms an opening for inserting a hand into the glove. A stretching mechanism is coupled substantially near or on the fold and is adapted to increase a size of the opening while donning the glove. At least a portion of the stretching mechanism is detachable. The stretching mechanism has an unstretched state and a stretched state, and the stretching mechanism is in the unstretched state when the glove is packaged.

DETAILED DESCRIPTION

One embodiment is a sterile glove with a stretching mechanism with a detachable handle that allows the glove to be donned without touching any of the wearable portion of the glove.

Figure 1:
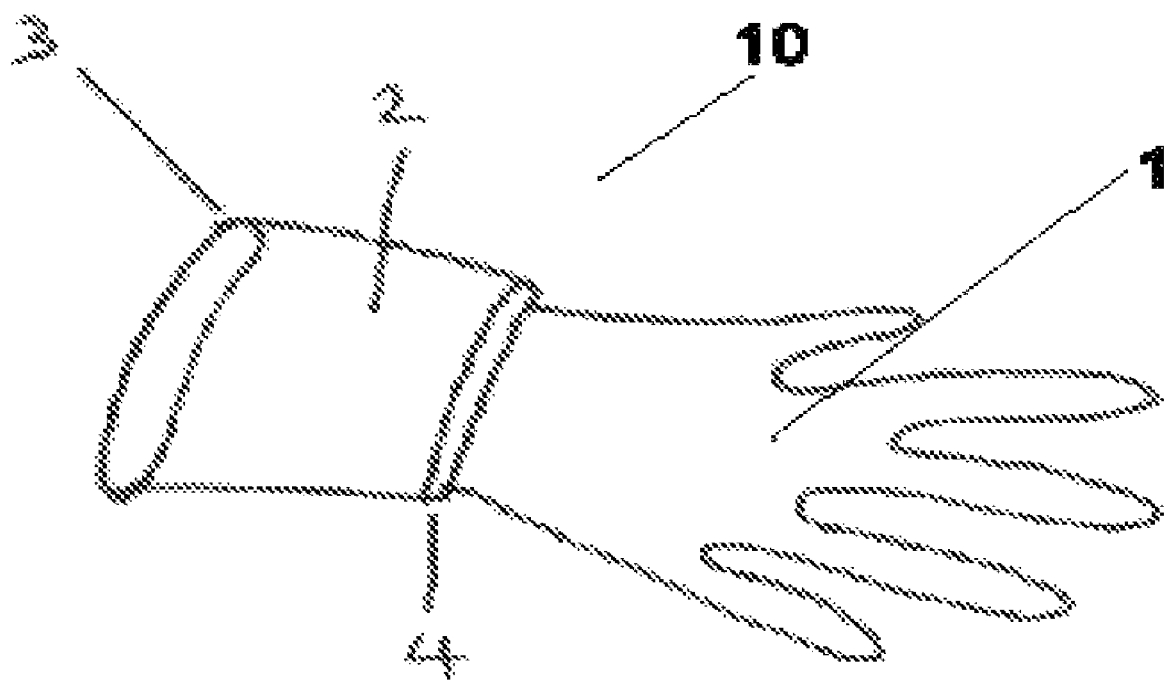
FIG. 1 is a perspective view of a prior art sterile glove as it is configured when it is removed from packaging and before being donned by a user.

FIG. 1 is a perspective view of a prior art sterile glove 10 as it is configured when it is removed from packaging and before being donned by a user. Glove 10 includes a cuff 2, a cuff rim 4, and a finger and hand portion 1. Cuff 2 of glove 10 as shown in FIG. 1 is in a state of being folded over at a fold 3 so that at least some of the inside surface is exposed as an "outer facing surface." This allows glove 10 to be held by touching only the region of the folded over cuff 2 that is near fold 3 thereby limiting contact to an area at some distance from cuff rim 4 and reducing the risk of contamination. The folded over cuff is unfolded before use of the glove. Use of the glove can include any activity after the glove has been donned. "Donning" includes all activities involved in inserting the hand into the glove and in unfolding its cuff.

Figure 2:
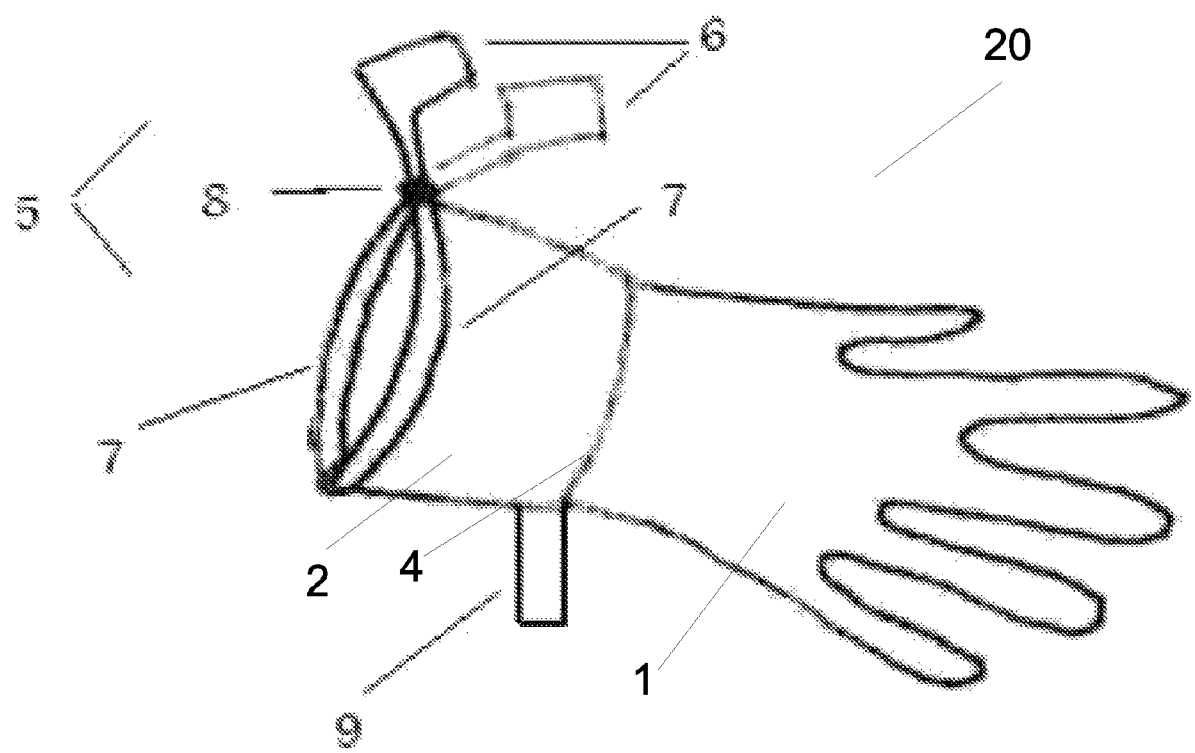
FIG. 2 is a perspective view of a sterile glove in accordance with one embodiment as it is configured when it is removed from its packaging or other storage means and before being donned by a user.

FIG. 2 is a perspective view of a sterile glove 20 in accordance with one embodiment as it is configured when it is removed from its packaging or other storage means and before being donned by a user. As with glove 10, glove 20 includes a folded over cuff 2 that has a cuff rim 4 and is folded over at a fold (not visible in FIG. 2), and a finger and hand portion 1. In its folded over state, at least part of the inside surface of cuff 2 is exposed as an "outer facing surface". Glove 20 further includes a stretching collar or "mechanism" 5 coupled to cuff 2 substantially near or on fold 3. Cuff fold 3 forms an opening for a user to insert a hand into glove 20. Glove 20 can further include a detachable tab 9, coupled substantially at or near cuff rim 4 and adapted for unfolding the folded cuff. Stretching mechanism 5 and detachable tab 9 can be contained within the glove's packaging to maintain sterile conditions. Stretching mechanism 5 is packaged in an unstretched state.

Figure 3:
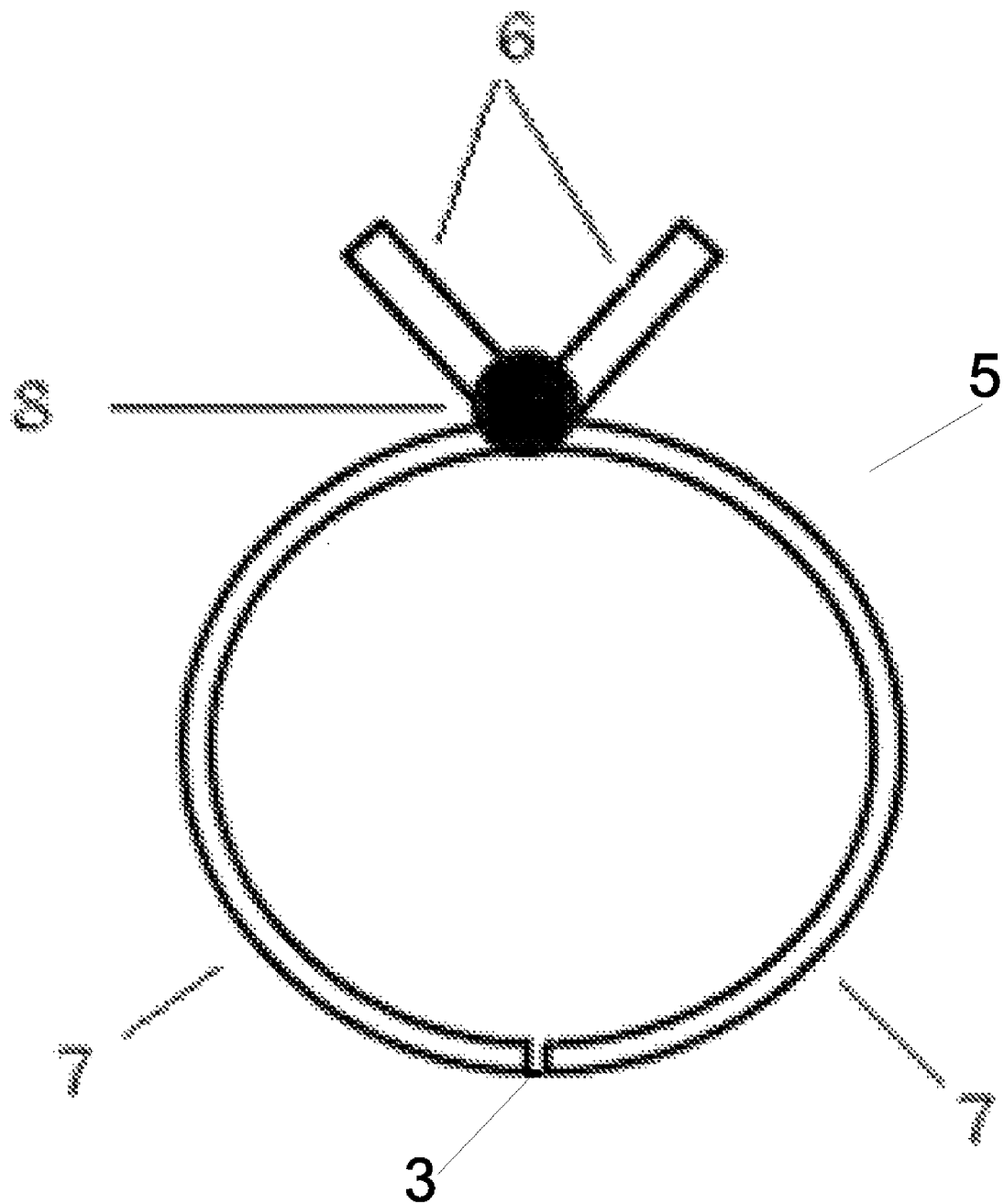
FIGS. 3 and 4 are side views of a stretching collar or mechanism in accordance with one embodiment.
Figure 4:
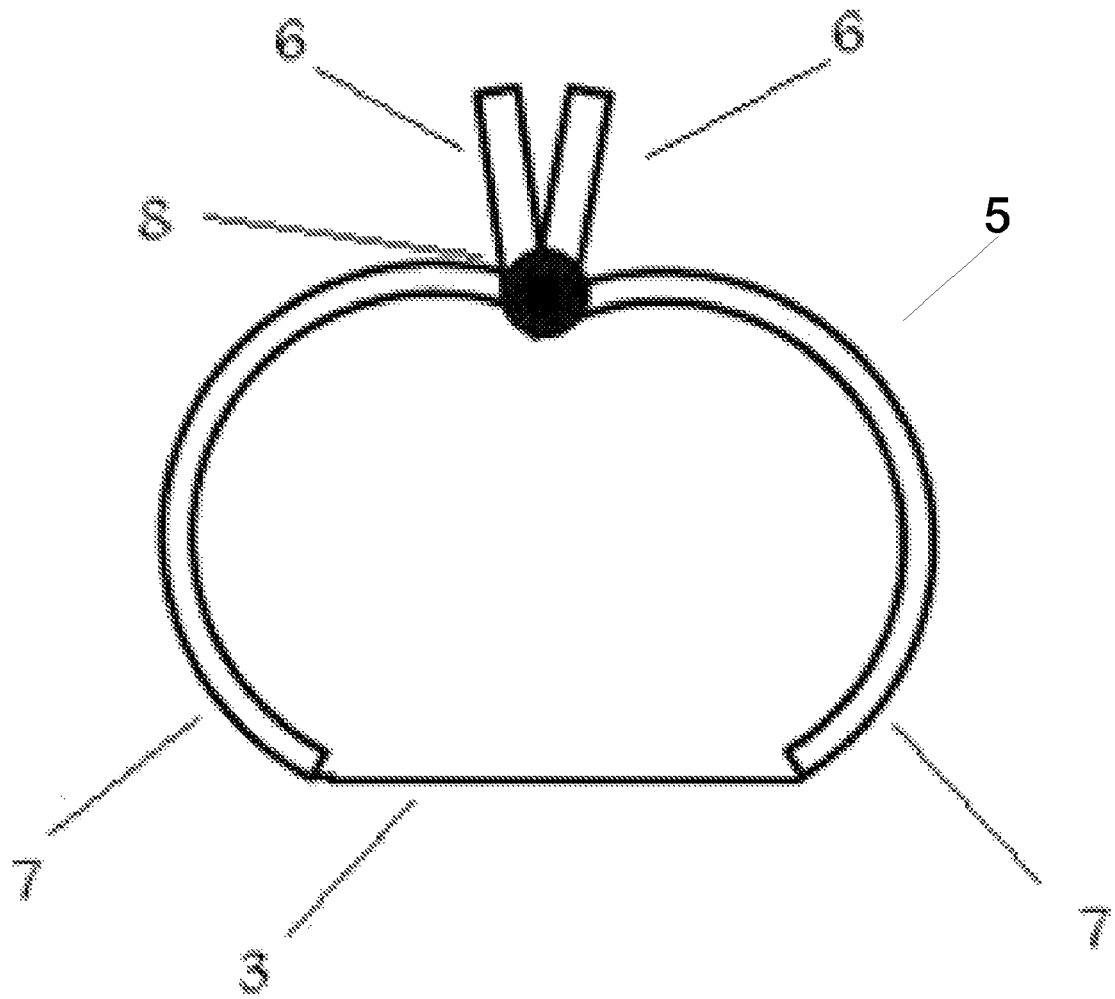

FIGS. 3 and 4 are side views of stretching collar or mechanism 5 in accordance with one embodiment. Stretching mechanism 5 includes a pair of handles 6, a pair of stretching arms 7 coupled to cuff fold 3 (an exposed portion of which is shown in FIGS. 3 and 4), and a pivot 8. In FIG. 3, handles 6 are in an opened position and fold 3 is in a minimal or unstretched state. In FIG. 4, handles 6 are in an closed position and fold 3 is in a stretched state. Therefore, in a stretched state, stretching mechanism 5 increases the opening of glove 20 to allow a user to more easily insert a hand.

Handles 6 extend sufficiently from the glove to be easily grasped by a user without touching any other part of the glove. Any object that can be suitably grasped can be used for handle 6, including a tab, loop, appendage, etc. (collectively referred to as a "handle"). In one embodiment, handles 6 are similar to the handles of conventional scissors or forceps. In one embodiment, sterile glove 20 is made with elastomeric impermeable material, such as latex, to prevent contamination.

In one embodiment, glove 20 is packaged in a sterile envelope (not shown) which when opened presents glove 20 to the user in an unstretched state as shown in FIGS. 2 and 3. The user can manipulate sterile glove 20 by grasping handles 6 between the user's thumb and forefinger. Stretching mechanism 5 can then be actuated by pressing the forefinger and thumb together, causing handles 6 to move to a closed position and arms 7 to open through pivot 8, as shown in FIG. 4. A second hand can then be inserted more easily through the cuff fold opening in its stretched state. Subsequently, all or part of the stretching mechanism 5 can be detached, leaving glove 20 securely on the second hand without any remaining surface having been in contact with the user's first hand.

In one embodiment, only the handles 6 are detached, leaving arms 7 and pivot 8 on the inside of glove 20 when cuff 2 is unfolded. In one embodiment, handles 6 include a pre-weakened area adjacent to pivot 8, which separates when pressure is applied in a suitable direction. In another embodiment, handles 6, arms 7 and pivot 8 are all detached prior to the cuff 2 being unfolded. In one embodiment, pivot 8 decouples if pulled in a direction away from finger and hand portion 1 of glove 20, enabling handles 6 to be used to pull arms 7 away from the glove 20. In this embodiment, the adhesive used to couple arms 7 to cuff 2 releases when pulled in a particular suitable direction.

In one embodiment, the folded cuff can be unfolded by grasping detachable tab 9 with the first hand and pulling in a direction away from hand and finger portion 1 of glove 20. Once cuff 2 is fully unfolded, tab 9 can be detached, leaving glove 20 in a fully donned state without any remaining surface having been in contact with the user's first hand. In one embodiment, no remaining surface of glove 20 has been in contact with anything that was not contained inside the glove's sterile packaging.

Handles 6, stretching arms 7 and pivot 8 can be of any shape or size that is convenient and can be made of a suitable material (e.g., a lightweight, strong and inexpensive plastic). Handles 6, stretching arms 7 and pivot 8 can be coupled to glove 20 by any suitable releasable known attachment mechanism that enables both a sufficiently strong attachment to allow cuff fold 3 to be stretched while donning and that also enables all, or at least the touched portion, of stretching mechanism 5 to be subsequently detached. Handles 6 can be oriented in any convenient direction. Stretching arms 7 can together extend along the whole of cuff fold 3, or partially along the length of cuff fold 3. Detachable tab 9 is of a sufficient length such that it can be easily grasped without contacting any other surface of the glove. Detachable tab 9 can be of any shape or size that is convenient and can be made of any suitable material, such as a lightweight plastic. Detachable tab 9 can be coupled to the cuff by any known releasable attachment means. In one embodiment, stretching mechanism 5 is designed to insure that the user cannot apply too much force to glove 20 while stretching to minimize risk of tearing, thereby improving safety.

Figure 5:
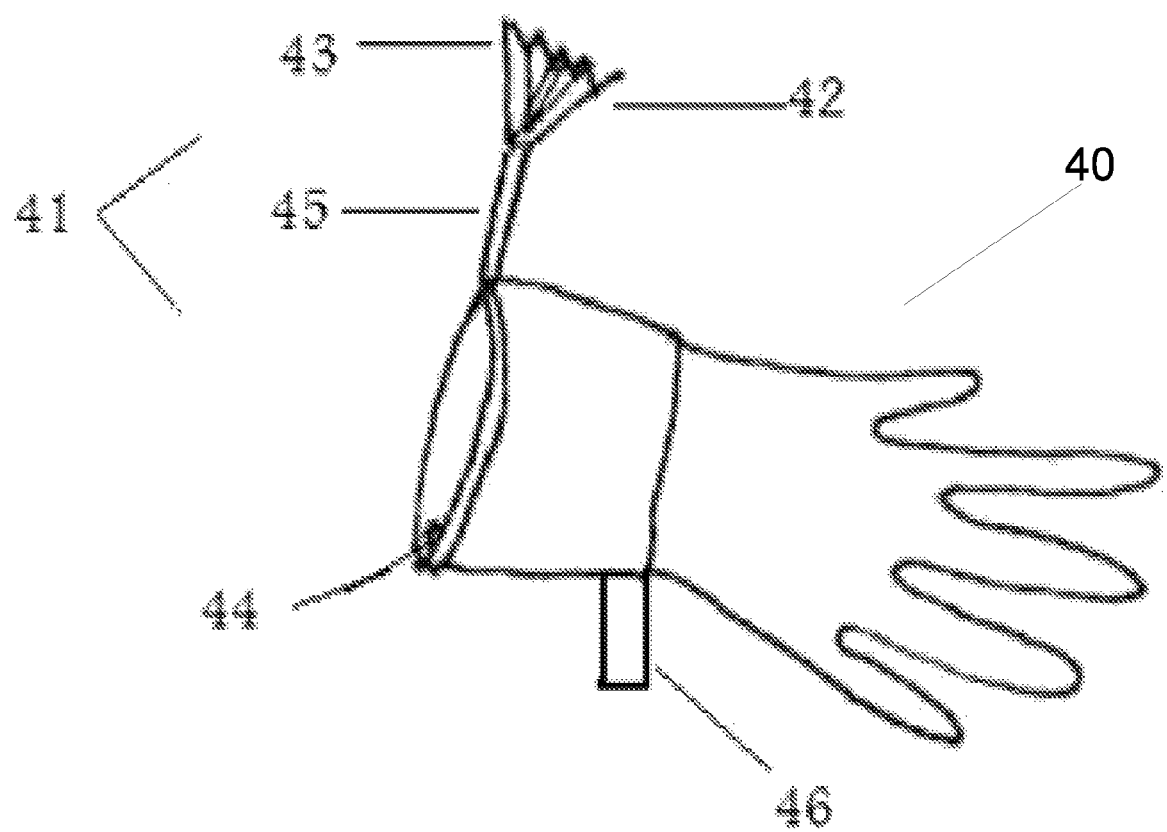
FIG. 5 is a perspective view of a sterile glove in accordance with one embodiment as it is configured when it is removed from packaging or other storage means and before being donned by a user.

FIG. 5 is a perspective view of a sterile glove 40 in accordance with one embodiment as it is configured when it is removed from packaging or other storage means and before being donned by a user. Sterile glove 40 has a pneumatic stretching mechanism 41 that includes a detachable handle 42, an air reservoir 43 and one or more airtight elastic stretching channels 44 coupled to cuff 2 on or substantially near fold 3 (not visible in FIG. 5). Air tight elastic channels 44 are in fluid communication with air reservoir 43 via an inflation channel 45. Air tight elastic channels 44 can be connected in fluid communication with air reservoir 43 via a one way valve. Glove 40 can further include a detachable tab 46, coupled substantially at or near cuff rim 4 and adapted for unfolding the folded cuff. Pneumatic stretching mechanism 41 and detachable tab 46 can be contained within the glove's packaging to maintain sterile conditions.

In one embodiment, glove 40 is packaged in an unstretched state and upon opening the sterile envelope (not shown), glove 40 can be grasped by a user by handle 42 using one hand. Handle 42 is of sufficient length to be easily grasped without touching any other part of glove 40. The contents of air reservoir 43 can be discharged into the airtight stretching channels 44. This inflates channels 44 and thereby stretches the cuff opening enabling easier insertion of a second hand. Handle 42, air reservoir 43 and inflation channel 45 can then be detached, leaving glove 40 on the other hand of the user, without any part of what remains having been touched by the user's first hand. The removal of handle 42, air reservoir 43 and inflation channel 45 can deflate the excess air pressure in stretching channels 44 to ensure glove cuff 2 is not in a stretched state during use. Stretching channels 44 can be either detachable, or can remain on the glove, since they will not be exposed when cuff 2 is unfolded. In one embodiment, the folded cuff can be unfolded by grasping the detachable tab 46 with the first hand and pulling in a direction away from the hand and finger portion of the glove. Once the cuff is full unfolded, tab 46 can be detached, leaving glove 40 in a fully donned state without any remaining surface having been in contact with the user's first hand. In one embodiment no remaining surface of the glove has been in contact with anything not contained inside the glove's sterile packaging.

Air reservoir 43 can be of a syringe type or a bellows type, or any other suitable type. Air reservoir 43 can be packaged empty and filled after opening the sterile envelope (e.g., by actuating bellows or by injecting the air from the syringe). Air reservoir 43 can be coupled to stretching channels 44 using a one way valve (not shown). Airtight stretching channels 44 can be constructed of the same material as glove 40. Airtight stretching channels 44 could be formed integrally during the formation of the glove cuff, or secured, for example, by a suitable adhesive, at a later point during manufacturing. Handle 42, air reservoir 43 and inflation channel 45 can be of any size and shape that is convenient and can be made of any suitable material (e.g., a lightweight plastic). Handle 42, air reservoir 43 and inflation channel 45 can be configured to be detached when twisted. Pneumatic stretching mechanism 41 can be configured to ensure only a safe amount of stretching is achievable, thereby reducing risks of tearing. Detachable tab 46 is of a sufficient length such that it can be easily grasped without contacting any other surface of the glove. Detachable tab 46 can be of any shape or size that is convenient and can be made of any suitable material, such as a lightweight plastic. Detachable tab 46 can be coupled to the cuff by any known releasable attachment means.

As disclosed, sterile gloves in accordance with embodiments of the present invention can be donned by users without any assistance and can be donned when a user has non-sterile hands, since at least the touched parts are detached prior to use of the glove. In one embodiment, no remaining surfaces of the glove have been contacted by anything that was outside the glove's sterile packaging.

Several embodiments are specifically illustrated and/or described herein. However, it will be appreciated that modifications and variations of the disclosed embodiments are covered by the above teachings and within the purview of the appended claims without departing from the spirit and intended scope of the invention. For example the above described stretching mechanisms are mechanical or pneumatic. However, any suitable stretching means can be used provided it can be packaged within a sterile envelope and can be actuated by the user only when required for donning. Embodiments are possible with a stretching means coupled on outside surface. Embodiments can be implemented for any elastic disposable sterile glove type.

What is claimed is:

1. A sterile glove comprising:
   a hand and finger portion;
   a cuff having an inside surface and an outside surface, wherein the cuff is adapted to be folded over at a fold when the glove is packaged in a sterile package and wherein the fold forms an opening for inserting a hand into the glove; and
   a stretching mechanism coupled substantially near or on the fold, wherein the stretching mechanism is adapted to increase a size of the opening while donning the glove and wherein at least a portion of the stretching mechanism is detachable, wherein the stretching mechanism comprises a pivot, a pair of handles, and a pair of arms;
   wherein the stretching mechanism has an unstretched state and a stretched state and the stretching mechanism is in the unstretched state when the glove is packaged.

2. The sterile glove of claim 1, wherein the stretching mechanism comprises a detachable handle.

3. The sterile glove of claim 1, wherein the handles are coupled to the arms through the pivot.

4. The sterile glove of claim 3, wherein the handles, stretching arms and pivot are configured so that when the handles are in an opened position the cuff fold is substantially unstretched and when the handles are in a closed position the cuff fold is stretched.

5. The sterile glove of claim 1, wherein the entire stretching mechanism is detachable.

6. The sterile glove of claim 1, wherein the stretching mechanism is coupled to the inside surface.

7. A method of packaging a sterile glove that comprises a hand and finger portion and a cuff having an inside surface, an outside surface and a cuff rim, the method comprising:
- folding the cuff at a fold so that at least a portion of the inside surface faces outward and wherein the fold forms an opening for inserting a hand into the glove; and
- coupling a stretching mechanism substantially near or on the fold, wherein the stretching mechanism is adapted to increase a size of the opening while donning the glove and wherein at least a portion of the stretching mechanism is detachable;
- wherein the stretching mechanism has an unstretched state and a stretched state and the stretching mechanism is in the unstretched state when the glove is packaged.

8. The method of claim 7, wherein the stretching mechanism comprises a detachable handle.

9. The method of claim 7, wherein the stretching mechanism comprises a pivot, a pair of handles, and a pair of arms.

10. The method of claim 7, wherein the stretching mechanism is pneumatic.

11. The method of claim 9, wherein the handles are coupled to the arms through the pivot.

12. The method of claim 11, wherein the handles, stretching arms and pivot are configured so that when the handles are in an opened position the cuff fold is substantially unstretched and when the handles are in a closed position the cuff fold is stretched.

13. The method of claim 10, wherein the stretching mechanism comprises a handle, an inflation channel, an air tight stretching channel and an air reservoir, wherein the air tight stretching channel is in fluid communication with the air reservoir via the inflation channel.

14. The method of claim 7, wherein the entire stretching mechanism is detachable.

15. The method of claim 7, wherein the stretching mechanism is coupled to the inside surface.

\* \* \* \* \*